United States Patent [19]
Conrad et al.

[11] Patent Number: 5,276,013
[45] Date of Patent: Jan. 4, 1994

[54] CONJUGATES OF BIOLOGICALLY STABLE POLYFUNCTIONAL MOLECULES AND POLYNUCLEOTIDES FOR TREATING SYSTEMIC LUPUS ERYTHEMATOSUS

[75] Inventors: Michael J. Conrad; Stephen Coutts, both of San Diego, Calif.

[73] Assignee: La Jolla Pharmaceutical Company, San Diego, Calif.

[21] Appl. No.: 914,869

[22] Filed: Jul. 15, 1992

Related U.S. Application Data

[63] Continuation-in-part of Ser. No. 494,118, Mar. 13, 1990, Pat. No. 5,162,515, which is a continuation-in-part of Ser. No. 466,138, Jan. 16, 1990, abandoned.

[51] Int. Cl.$^5$ .............. A61K 31/00; A61K 31/70; C07H 17/00
[52] U.S. Cl. .................. 514/2; 514/44; 536/24.2; 424/78.02; 424/78.24; 424/78.31
[58] Field of Search .............. 536/24.2; 514/2, 44, 514/885; 424/78.02, 78.24, 78.31

[56] References Cited

U.S. PATENT DOCUMENTS

| | | | |
|---|---|---|---|
| 4,191,668 | 3/1980 | Katz | 260/6 |
| 4,220,565 | 9/1980 | Katz | 260/6 |
| 4,650,675 | 3/1987 | Borel et al. | 424/85 |
| 4,751,181 | 6/1988 | Keene | 355/70 |
| 5,126,131 | 6/1992 | Dintzis et al. | 424/88 |

FOREIGN PATENT DOCUMENTS

WO86/04093 7/1986 PCT Int'l Appl. .
WO92/11029 7/1992 PCT Int'l Appl. .

OTHER PUBLICATIONS

Eshhar Z., et al., *J. Immunol.* (1975) 114(2):872-876.
Borel Y., et al., *Science* (1973) 182:76-78.
Parker L., et al., *J. Immunol.* (1974) 113(1):292-297.
Borel H., et al., *Ann. N.Y. Acad. Sci.* (1986) 475:296-306.
Papalian M., et al., *J. Clin. Invest.* (1980) 65:469-477.
Stollar B., et al., *J. Clin. Invest.* (1980) 66:210-219.
Borel Y., et al., *J. Clin, Invest.* (1988) 82:1901-1907.
Agrawal S., et al., *Nucl. Acids Res.* (1986) 14(15):6227-6245.
Kremsky J., et al., *Nucl. Acids Res.* (1987) 14(7):2891-2909.

*Primary Examiner*—John W. Rollins
*Attorney, Agent, or Firm*—Morrison & Foerster

[57] ABSTRACT

Chemically defined conjugates of biologically stable valency platform molecules, such as copolymers of D-glutamic acid and D-lysine or polyethylene glycol, and polynucleotide duplexes of at least 20 base pairs that have significant binding activity for human lupus anti-dsDNA autoantibodies. The duplexes are preferably homogeneous in length structure and are bound to the valency platform molecule via reaction between a functional group located at or proximate a terminus of each duplex and functional groups on the valency platform molecule. These conjugates are tolerogens for human systemic lupus erythematosus.

33 Claims, 9 Drawing Sheets

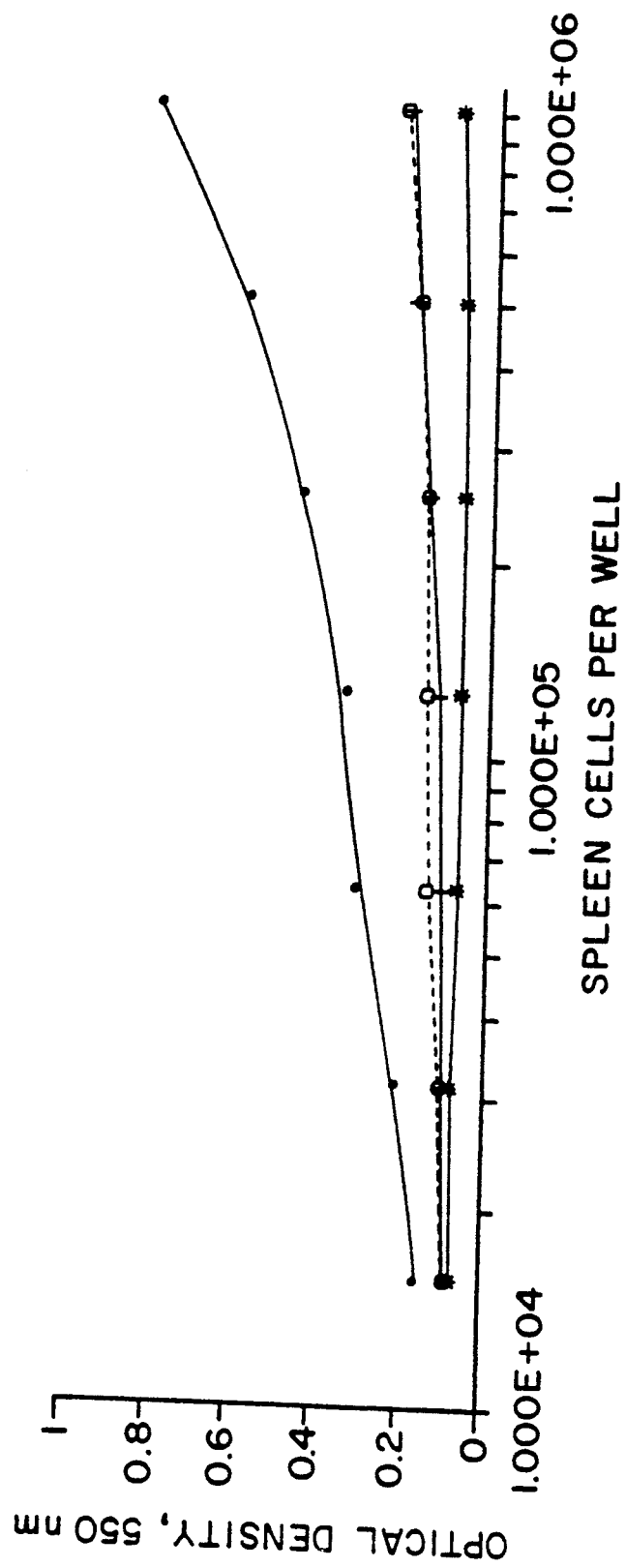

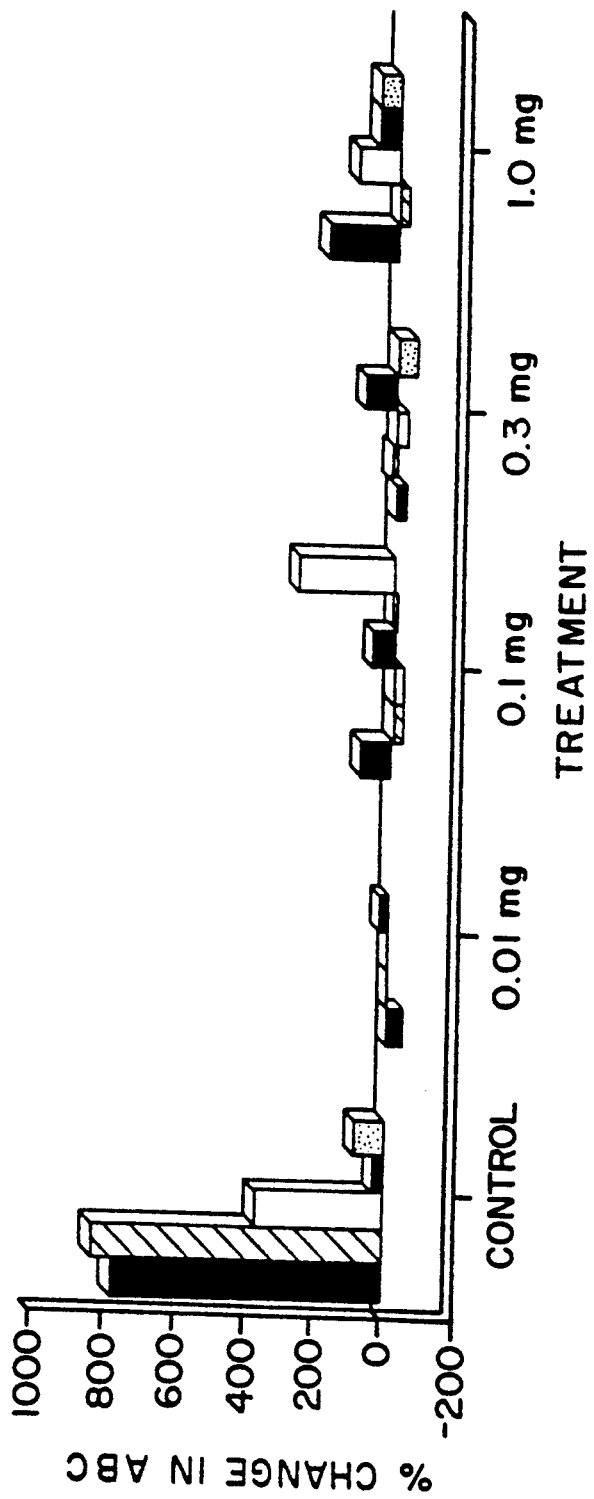

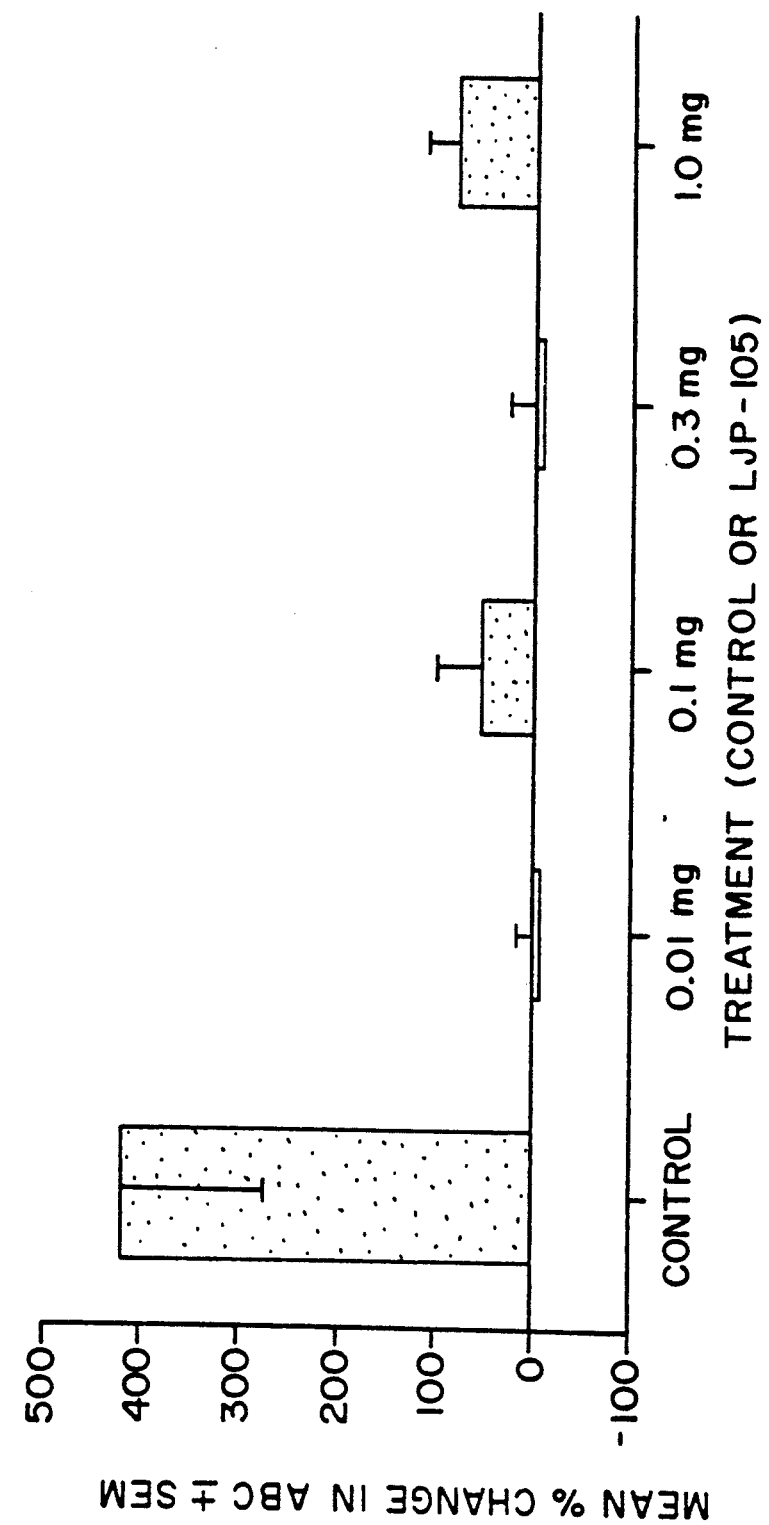

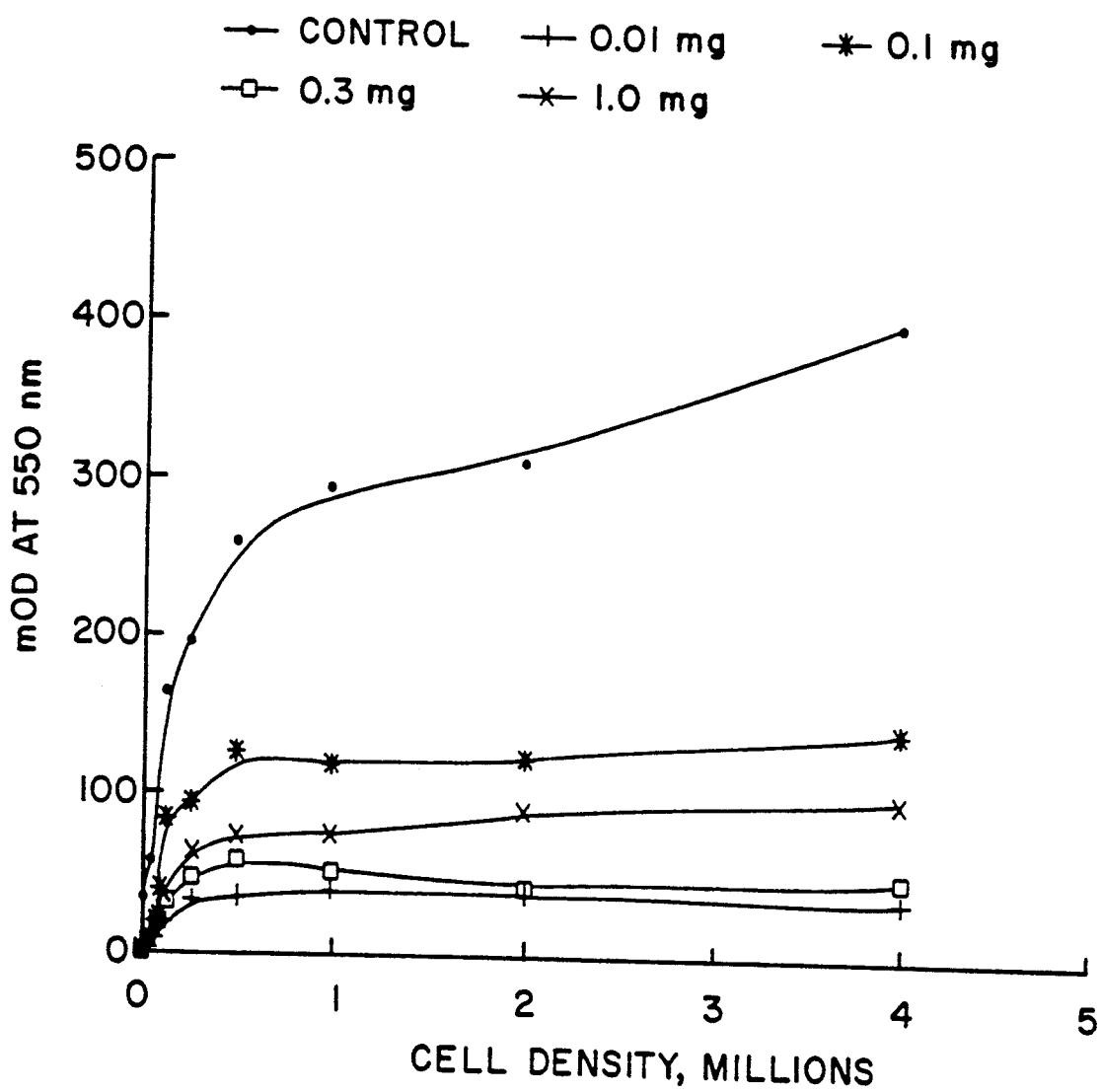

CONJUGATES OF BIOLOGICALLY STABLE POLYFUNCTIONAL MOLECULES AND POLYNUCLEOTIDES FOR TREATING SYSTEMIC LUPUS ERYTHEMATOSUS

CROSS-REFERENCE TO RELATED APPLICATIONS

This application is a continuation-in-part (CIP) of U.S. Ser. No. 07/494,118, filed 13, Mar. 1990, now U.S. Pat. No. 5,162,515 which in turn is a CIP of U.S. Ser, No. 07/466,138, filed 16 Jan. 1990, now abandoned. The disclosures of each of these parent applications is incorporated herein by reference.

DESCRIPTION

1. Technical Field

This invention relates to compositions for treating the autoimmune disease systemic lupus erythematosus (SLE or "lupus"). More particularly it relates to conjugates of biologically stable valency platform molecules such as polymers, preferably copolymers of glutamic acid (represented herein by the single letter designation "E") and D-lysine (represented herein by the single letter designation "K") or polyethylene glycol (PEG) and certain polynucleotides that have been found to be effective for inducing tolerance to autoantigens involved in SLE. The preferred polymers are represented herein by the designation "D-EK" or "PEG."

2. Background

"Immune tolerance" describes the mechanism leading to the very long-lived and often permanent form of immune suppression that keeps individuals from reacting with their own tissues. It is believed that immune tolerance to self-antigens (autoantigens) is normally established during neonatal development and persists throughout an animal's life. Not surprisingly, however, this scheme is sometimes imperfect and some individuals, typically later in life, acquire autoimmune diseases. One such disease is SLE. It is characterized by the production of autoantibodies to the individual's DNA, and results in the progressive inflammatory degeneration of the kidneys SLE is typically treated by administration of broad spectrum, nonspecific immunosuppressants such as cyclophosphamide or prednisone. Because these drugs often suppress all aspects of the immune system, they suppress its required and beneficial functions as well as the malfunction causing SLE. Thus, they must be administered with extreme caution and are not always appropriate to manage the disease on a continuing basis. Furthermore, individuals who are generally and severely immunosuppressed by such drug treatment are at risk for other complications, especially infectious diseases.

A preferable approach to SLE treatment would be to administer a drug that is capable of reestablishing immune tolerance to the autoantigens involved in SLE without affecting the normal functions of the immune system. Unfortunately, there is no current way of treating SLE, or for that matter any autoimmune disorder, that is benign and specific to the disease-associated autoantigens. The conjugates of the invention are a means for providing such treatment for SLE.

Benacerraf, Katz, and their colleagues investigated and described the use of conjugates of D-glutamic/D-lysine, referred to as D-GL in earlier literature, (herinafter "D-EK"); with haptens and various antigens to induce specific immune tolerance. Their initial studies involved conjugates of the synthetic hapten 2,4-dinitrophenyl (DNP) in guinea pigs and mice and showed that the conjugates could induce tolerance to DNP. These initial studies were extended to other haptens/antigens such as ragweed antigen E and benzylpenicilloyl (BPO). See U.S. Pat. Nos. 4,191,668 and 4,220,565.

U.S. Pat. No. 4,191,668 (Example IV) describes the preparation of conjugates of D-EK and oligonucleotides isolated from DNAse 1-digested calf thymus DNA. The oligonucleotides were characterized as being composed of "fewer than 10 nucleotides." Although column 11 of U.S. Pat. No. 4,191,668 indicates that its invention has therapeutic value for treatment of autoimmune disease and mentions SLE, no data are presented on the immunological effects of the mentioned D-EK-oligonucleotide conjugates.

Katz and his colleagues also investigated the potential of nucleoside-D-EK conjugates to induce tolerance to nucleic acid determinants. Eshar et al. *J Immunology* (1975) 114:872–876. In this regard the individual nucleosides were widely believed to be the principal determinants of specificity in lupus antisera. They administered conjugates of D-EK copolymer and four ribonucleosides to SJL or Balb/c strain mice and subsequently immunized the treated mice with a keyhole limpet hemocyanin (KLH)-ribonucleoside conjugates. In both strains the anti-nucleoside antigen binding capacity of the sera dropped to barely detectable levels. While these studies showed such conjugates could produce immune tolerance to nucleosides, they did not show such conjugates to be effective in treating SLE.

Other investigators have studied conjugates of nucleosides or DNA with other carriers. Borel et al. (*Science* (1973) 182:76) evaluated the ability of isogenic mouse IgG-nucleoside conjugates to reduce the antibody response to denatured DNA in young animals of the NZB mouse strain. This strain is used as a model for some autoimmune phenomena. They tend to produce antibodies to nucleic acid determinants which form immune complexes that lodge in the kidneys and lead to glomerular nephritis. In these studies the treated animals produced significantly reduced levels of anti-denatured DNA antibodies and exhibited less membranous glomerulonephritis than control and free nucleoside-treated animals. In separate studies Parker et al. (*J. Immunol.* (1974) 113:292) evaluated the effect of denatured DNA conjugated to poly-D-lysine and/or cyclophosphamide on the progression of the above-described syndrome in NZB mice. These studies demonstrated a significant increase in survival and a significant decrease in DNA binding capacity for treated animals as compared to controls. Neither of these studies, however, was directed to producing tolerance to double-stranded DNA (dsDNA) which appears to be principal autoantigen involved in human SLE.

In a later article (*Ann NY Acad Sci* (1986) 475:296–306) Borel et al. suggest that the realization of specific immunotherapy for SLE has been hampered by "an inability to link DNA fragments to soluble protein." Citing prior work by Stoller (Papalian et al., *J Clin Invest* (1980) 65:469 and Stoller and Papalian, *J Clin Invest* (1980) 66:210), the authors state that a minimum size of at least 10–40 base pairs of DNA is necessary to bind anti-DNA antibody made in SLE patients. The article describes oligonucleotide-immunoglobulin conjugates made by linking a native DNA fraction "somewhat larger than 10 base pairs" using glutaraldehyde as a linking agent. FIG. 2 of the article describes the studies used to select the DNA fraction. That figure reports the reactivity of the various DNA fractions linked to sheep red blood cells via glutaraldehyde with anti-DNA antibodies in (NZB×NZW)F1 (hereinafter $BWF_1$) sera. In those tests the fraction designated "70–80" was the most reactive. The size of that fraction is described as being "somewhat larger" than fraction 81–101 which corresponded to "about 10 oligonucleotides." The next larger fraction to 70–80, designated "40–69", exhibited significantly reduced reactivity relative to fraction 70–80. It will be appreciated that the fraction "somewhat larger than 10 base pairs" is heterogeneous in size and, because of the linking procedure, is linked to the immunoglobulin at a random site on the chain. Furthermore, because a bifunctional linking agent is used it is likely that some degree of cross-linking occurred in the coupling reaction. Thus, the conjugate described in this article is not a chemically defined moiety in the sense that (a) the sequence of the oligonucleotide is not defined, (b) the length of the oligonucleotide is not specified, (c) the oligonucleotide fraction contains chains of varying length, (d) the site of attachment to the immunoglobulin along the oligonucleotide chain length is random, (e) there is some degree of cross-linking, and (f) unconjugated but cross-linked oligonucleotides could not be separated from conjugated material.

Borel et al (*J Clin Invest* (1988) 82:1901–1907 or U.S. Pat. No. 4,650,675) have described in vitro studies using conjugates of human immunoglobulin linked to either total DNA digest (designated $N_{10-100}$) or a 20–30 base pair fraction (designated $N_{20-30}$) using glutaraldehyde as a coupling agent. The conjugates were reported to exhibit tolerogenic properties in vitro on peripheral blood lymphocytes (PBLs) from SLE patients. These conjugates, however, like those reported in their 1986 article, are also produced with heterogeneous mixtures of oligonucleotides using methods that produce non-specifically cross-linked networks. Hence, neither the chemistry nor the biological activity of these conjugates would be sufficiently reproducible to permit them to be approved as pharmaceuticals.

DISCLOSURE OF THE INVENTION

In contrast to the above described art applicants have developed chemically defined conjugates of biologically stable and compatible valency platform molecules and polynucleotide duplexes that are tolerogens for human SLE. These duplexes are defined with respect to sequence, length, site of attachment to the platform, helical structure, and binding affinity to human SLE anti-dsDNA autoantibodies. Accordingly, their chemistry and tolerogenic activity are reproducible to a degree that makes these conjugates amenable to quality control and approval as pharmaceuticals.

Thus, one aspect of the invention is a conjugate of a biologically stable valency platform molecule and a multiplicity of polynucleotide duplexes of at least about 20 base pairs each bound to the platform molecule, and significant binding activity for human SLE anti-dsDNA autoantibodies. In a preferred embodiment of these conjugates, the duplexes are substantially homogeneous in length and are coupled to the platform at or proximate (i.e. within about 5 base pairs) one of their ends such that each duplex forms a pendant chain of at least about 20 base pairs measured from the site of attachment of the duplex to the platform molecule to the free end of the chain.

Pharmaceutical compositions containing these conjugates and methods for treating SLE that employ these conjugates are other aspects of the present invention.

Still another aspect is a conjugate of (a) a biologically stable valency platform molecule and (b) a multiplicity of polynucleotide duplexes each and all of which is bound to the valency platform molecule by a functional group located at or proximate a terminus of one of the strands of the duplex, said conjugate being a human SLE tolerogen.

A further aspect of the invention is a method for making the conjugates described above comprising: reacting a multiplicity of single-stranded polynucleotides each of which is at least about 20 nucleotides in length and has a functional group at or proximate one of its termini that reacts with functional groups on the valency platform molecule to form a conjugate and annealing complementary single-stranded polynucleotides to the single-stranded polynucleotides conjugated to the valency platform molecule to form pendant chains of double-stranded DNA.

BRIEF DESCRIPTION OF THE DRAWINGS

FIGS. 5–8 are graphs of data obtained from the tests described in Example 5.

MODES FOR CARRYING OUT THE INVENTION

Figure 1:
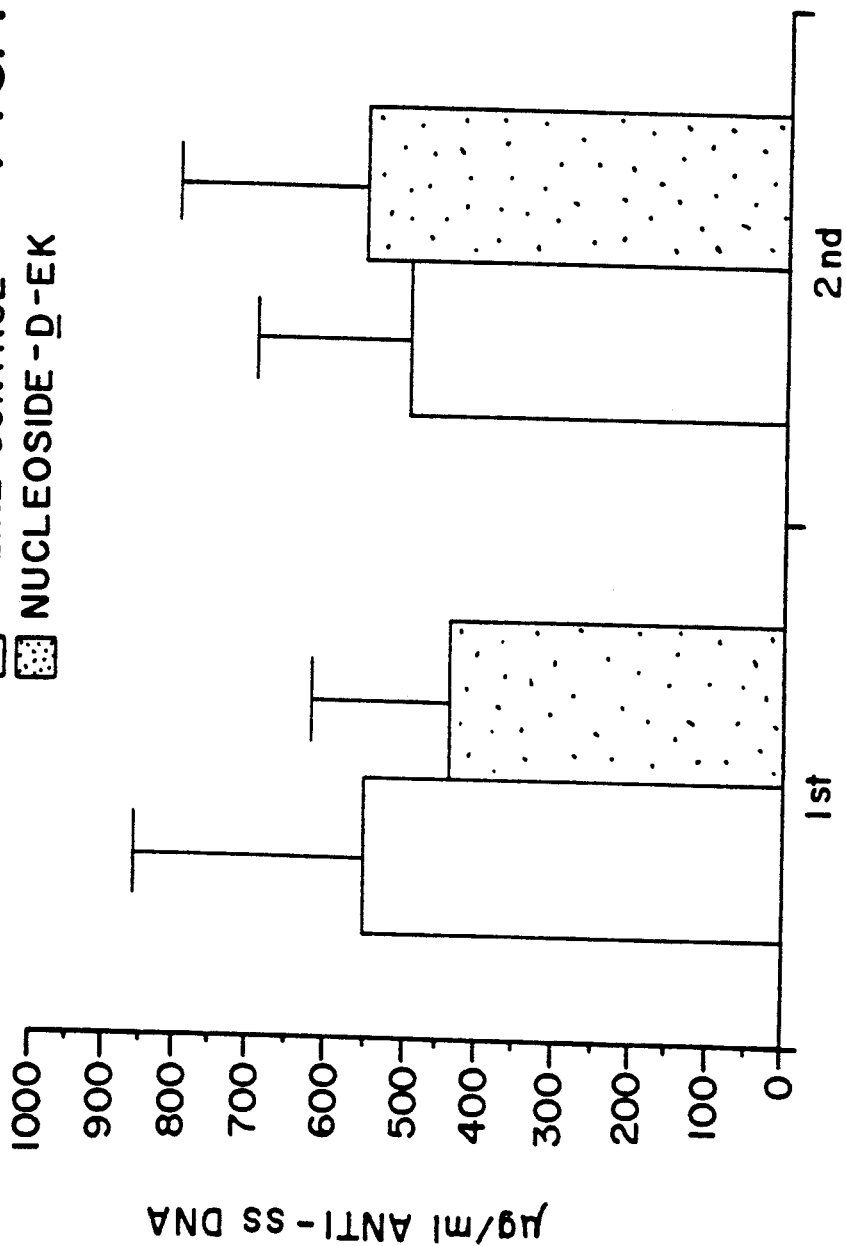
FIG. 1 is a graph of data obtained from the tests described in Example 1.

The valency platform molecule component of the conjugate, typically a polymer, is biologically stable; that is, it exhibits an in vivo excretion half-life of days to months. These molecules are also substantially nonimmunogenic (i.e., they exhibit no or only mild immunogenicity when administered to animals), non-toxic at the doses given and are preferably composed of a synthetic single polymer chain of defined composition. They provide a stable, non-immunogenic, non-toxic polyfunctional substrate to which a multiplicity of oligonucleotide duplexes may be attached covalently. They will normally have an average molecular weight in the range of about 500 to about 200,000, preferably 500 to 20,000. Examples of such polymers are PEG, poly-D-lysine, polyvinyl alcohol, polyvinylpyrollidone, immunoglobulins, and D-EK. Particularly preferred polymers are D-EKs or PEGs having a molecular weight of about 1,000 to about 20,000.

The synthetic polynucleotide duplexes that are coupled to the biologically stable valency platform molecule are composed of at least about 20 bp and preferably 20–50 bp. Preferably the duplexes are substantially homogeneous in length; that is, the variation in length in the population will not normally exceed about ±20%, preferably ±10%, of the average duplex length in base pairs. They are also preferably substantially homogeneous in nucleotide composition; that is, their base composition and sequence will not vary from duplex to duplex more than about 10%. Most preferably they are entirely homogeneous in nucleotide composition from duplex to duplex. In terms of composition, the preferred synthetic or recombinant dsDNA is preferably composed of strands of complementary repeating units of 2-4 bases (i.e., a repeating dimer, trimer or tetramer) such as

| | |
|---|---|
| $(AC)_n$ | (dimer) |
| $(TG)_n$ | |
| $(TAC)_{n'}$ | (trimer) |
| $(ATG)_{n'}$ | |
| $(GCTA)_{n''}$ | (tetramer) |
| $(CGAT)_{n''}$ | | where n, n' and n" are integers selected to provide the desired number of base pairs. Polynucleotides composed of isomeric dimers, e.g., poly d(AC):poly d(GT) and poly d(AG):poly d(CT) are most preferred.

Based on circular dichroic (CD) spectra interpretation, it is believed that the duplexes that are useful in the invention assume a B-DNA type helical structure. It should be understood that it is not intended that the invention be limited by this belief and that the duplexes may, upon more conclusive analysis assume Z-DNA and/or A-DNA type helical structures. B-DNA forms right-handed helices having base pairs nearly perpendicular to the long helical axis of the other two types of DNA helices. The helical structures of the different types of DNA may be characterized by the circular dichroic (CD) spectra. The CD spectra of the B form of DNA exhibits (1) positive dichroic bands associated with right-handed helicity in the portions of the spectrum below 250 nm but separated from the positive long wavelength dichroic band above 206 nm by a significant minimum at a wavelength between 240 and 260 nm, and (2) a broad singlet peak above 250 nm with a maximum blue shifted relative to the maxima seen in spectra of the A forms of RNA and DNA and centered at a wavelength between 270 and 290 nm. By way of general comparison of the other two helical forms of DNA, Z-DNA is distinguished by its tight left-handed helical twist with base pairs not positioned symmetrically around the helical axis and A-DNA forms a more open, right-handed helix on which the base pairs are obliquely oriented to the long helical axis and are pulled away from the helix core.

These polynucleotide duplexes may be synthesized from native DNA or synthesized by chemical or recombinant techniques. Naturally occurring or recombinantly produced dsDNA of longer length may be digested (e.g., enzymatically, chemically or by mechanical shearing) and fractionated (e.g., by agarose gel or Sephadex column) to obtain polynucleotides of the desired length.

Alternatively, pairs of complementary single-stranded polynucleotide chains up to about 70 bases in length are readily prepared using commercially available DNA synthesizers and then annealed to form duplexes by conventional procedures. Synthetic dsDNA of longer length may be obtained by enzymatic extension (5,-phosphorylation followed by ligation) of the chemically produced shorter chains.

The polynucleotides may also be made by molecular cloning. For instance, oligonucleotides of desired length and sequence are synthesized as above. These oligonucleotides may be designed to have appropriate termini for ligation into specific restriction sites. Multiple iterations of these oligomers may be ligated in tandem to provide for multicopy replication. The resulting construct is inserted into a standard cloning vector and the vector is introduced into a suitable microorganism/cell by transformation. Transformants are identified by standard markers and are grown under conditions that favor DNA replication. The polynucleotides may be isolated from the other DNA of the cell/microorganism by treatment with restriction enzymes and conventional size fractionation (e.g., agarose gel, Sephadex column).

Alternatively, the oligonucleotides may be replicated by the polymerase chain reaction (PCR) technology. Saiki, R. K, et al., *Science* (1985) 230:1350; Sacki, et al., *Science* (1988) 239:487; Sambrook, et al., *In Molecular Cloning Techniques: A Laboratory Manual*, Vol. 12, p 14.1-14.35 Cold Spring Harbor Press (1989).

In contrast to the prior art conjugates, each polynucleotide duplex employed in the present invention exhibits significant binding activity with SLE antisera. Preferably, they are substantially homogeneous in length. In this regard the prior art polynucleotides were heterogeneous in length and composed of a mixture of chains, some or all of which were too short to exhibit such activity. Polynucleotides may be screened for binding activity with SLE antisera by the assays described in the examples. The modified Farr assay in which binding activity may be expressed as $I_{50}$ (the polynucleotide concentration in molar nucleotides resulting in half-maximal inhibition) is a preferred assay. Polynucleotide duplexes having an $I_{50}$ of less than about 500 nM, preferably less than 50 nM, are deemed to have significant binding activity and are, therefore, useful for making the conjugates of this invention.

The polynucleotides are bound to the platform molecule in a manner that preserves their binding activity. This is done by coupling the polynucleotide to the platform molecule at a predetermined site on the polynucleotide chain such that the polynucleotide forms a pendant chain of at least about 20 base pairs measured from the coupling site to the free (unattached) end of the chain. In contrast, the glutaraldehyde coupling technique taught by the Borel et al. references causes coupling at random sites along the chain and cross-linking. Thus, using the Borel et al. technique, chains of greater than 20 base pairs may be coupled at an intermediate site on the chain to form pendant chains of substantially less than 20 base pairs in length or chains may be coupled together to form cross linked networks of undefined size.

Preferably the polynucleotide duplexes of the invention conjugates are coupled or conjugated to the platform molecule at a site at or proximate one of their ends. Several conjugation strategies are available for so attaching the oligonucleotides to the platform. The polynucleotide may be coupled to the platform molecule at the 3' end of the polynucleotide via a morpholino bridge formed by condensing an oxidized 3' terminal ribose on one of the strands of the polynucleotide with a free amino group on the platform molecule and then subjecting the adduct to reducing conditions to form the morpholino linkage. Such coupling requires the platform molecule to have at least an equal number of free amino groups (e.g., the epsilon amino groups of D-EK) to the number of polynucleotide duplexes to be bound to the platform molecule. The synthesis of such a conjugate is carried out in two steps. The first step is coupling one strand of the polynucleotide duplex to the platform molecule via the condensation/reduction reaction described above. The oxidized 3' terminal ribose is formed on the single polynucleotide strand by treating the strand with periodate to convert the 3' terminal ribose group to an oxidized ribose group. The single-stranded polynucleotide is then added slowly to an aqueous solution of the platform molecule of about pH 6.0 to 8.0 at 2°–8° C. The molar ratio of polynucleotide to platform molecule in all the conjugation strategies will normally be in the range of about 2:1 to about 30:1, preferably about 4:1 to 6:1. In this regard, it is preferable that the conjugate not have an excessively large molecular weight as large molecules, particularly those with repeating units, of m.w. >2,000,000 may be T-independent immunogens. See Dintzis et al., *J. Immun.* (1983) 131:2196 *J. Immun.* (1989) 143:1239. During or after the condensation reaction (normally a reaction time of 24 to 48 hr), a strong reducing agent, such as sodium cyanoborohydride, is added to form the morpholino group. The complementary strand of the duplex is then added to the conjugate and the mixture is heated and slowly cooled to cause the strands to anneal. The conjugate may be purified by gel permeation chromatography.

Another strategy involves forming terminal aldehyde functionalities on the oligonucleotides and using those functionalities to couple the oligonucleotide to the platform molecule via reactive functional groups thereon. Advantage may be taken of the fact that gem, vicinal diols, attached to the 3' end of the oligonucleotide, may be oxidized with sodium periodate to yield aldehydes which can condense with functional amino groups of the platform molecule. When the diols are in a ring system, e.g., a five-membered ring, the resulting condensation product is a heterocyclic ring containing nitrogen, e.g., a six-membered morpholino or piperidino ring. The imino-condensation product is stabilized by reduction with a suitable reducing agent; e.g., sodium borohydride or sodium cyanoborohydride. When the diol is acyclic, the resulting oxidation product contains just one aldehyde and the condensation product is a secondary amine.

The vicinal diol strategy also may be followed for 5'-terminal linkers. This is accomplished by making cyanoethylphosphoramidite derivatives of a third hydroxy group on a triol, where the remaining hydroxy groups are vicinal; e.g., 3,4-cis dihydroxy, 1-hydroxymethyl cyclopentane. In this specific case, the vicinal dihydroxy groups are blocked with dimethylsilane, and the primary hydroxy group is derivatized with 2-cyanoethyl-N,N-diisopropylchlorophosphoramidite. The resulting derivative is used in the last step of standard oligonucleotide synthesis, and becomes the 5-terminal residue. After deblocking the oligonucleotide and removing the dimethylsilyl group with fluoride ion, acid, or base, the vicinal diol can be oxidized with periodate and condensed with amine groups as above. A similar strategy could be followed for cyclic triols to be used as 5'-terminal linkers.

Another procedure involves introducing alkylamino or alkylsulfhydryl moieties into either the 3' or 5' ends of the oligonucleotide by appropriate nucleotide chemistry, e.g., phosphoramidate chemistry. The nucleophilic groups may then be used to react with a large excess of homobifunctional cross-linking reagent, e.g., dimethyl suberimidate, in the case of alkylamine derivatives, or an excess of heterobifunctional cross-linking reagent, e.g., m-maleimidobenzoyl-N-hydroxysuccinimide ester (MBS) or succinimidyl (4-iodoacetyl) aminobenzoate (SIAB), for the alkylsulfhydryl derivatives. Once excess cross-linker is removed, the oligonucleotide derivatives are reacted with amino groups on the platform molecule. Alternatively, the sulfhydryl group may be reacted with an electrophilic center on the platform, such as a maleimide or α-haloacetyl group or other appropriate Michael acceptor.

Still another strategy employs modified nucleosides. Suitable deoxynucleoside derivatives can be incorporated, by standard DNA synthetic chemistry, at desired positions in the oligonucleotide, preferably on the 5' or 3' ends. These nucleoside derivatives may then react specifically and directly with alkylamino groups on the platform molecule. Alternatively, side reactions seen with the above-described dialdehyde chemistry, such as amine catalyzed beta-elimination, can be circumvented by employing appropriate nucleoside derivatives as the 3' terminus of the chain to be attached. An example of this is 5' methylene extension of ribose; i.e., a 5' (2-hydroxyethyl) group instead of a 5' hydroxymethyl group. An alternative would be to use a phosphonate or phosphinate linkage for the 3' terminal dinucleotide of the oligonucleotide to be attached to the platform molecule.

The ability of the conjugates to act as SLE tolerogens and specifically suppress production of anti-dsDNA antibodies may be evaluated in the murine model described in the examples.

The conjugates will normally be formulated for administration by injection, (e.g., intraperitoneally, intramuscularly, etc.). Accordingly, they will typically be combined with pharmaceutically acceptable aqueous carriers such as saline, Ringer's solution, dextrose solution, and the like. The conjugate will normally constitute about 0.0% to 10% by weight of the formulation. The conjugate is administered to an individual in amounts sufficient to at least partially reestablish tolerance to the autoantigens causing SLE. Such amounts are sometimes herein referred to as "therapeutically effective" amounts. The particular dosage regimen i.e., dose, timing and repetition, will depend upon the particular individual, and that individual's medical history. Normally a dose of about 1 to 1000 $\mu$g conjugate/kg body weight will be given. Repetitive administrations may be required to achieve and/or maintain a state of immune tolerance.

The following examples further illustrate the invention and its unexpectedness relative to the prior art. These examples are not intended to limit the invention in any manner.

EXAMPLE 1

Testing of Conjugates of D-EK and Individual Nucleosides

As indicated previously, the development of the invention conjugates was preceded by tests that showed that conjugates of D-EK and individual nucleosides did not tolerize the anti-DNA response in the murine model for SLE ((NZB×NZW)F$_1$ strain mice).

Lots of D-EK were obtained from BioMakor/Yeda (Rehovet, Israel). Their relative molecular weights were standardized against known globular proteins by HPLC gel permeation chromatography and the material was desalted and sized by exhaustive dialysis in 25 Kd cutoff tubing against 0.1M K$_2$HPO$_4$, pH 9.5. The material was then dialyzed twice against water. This material is stored in 0.1M K$_2$HPO$_4$, pH 9.5 buffer at 4° C. The weight average molecular weights of the products were determined by physical methods including sedimentation equilibrium, PAGE, and HPLC-GPC and low-angle scattering and found to be approximately 28,000. Amino acid analysis by acid hydrolysis showed the copolymer was 60% glutamic acid and 40% lysine.

Conjugates of the D-EK and riboadenosine, riboguanosine, ribocytosine and ribothymidine were prepared essentially as described in Eshar et al., *J. Imm.* (1975) 114:872. A mixture of equal parts of each of these conjugates (designated nucleoside-D-EK) was used in the following tests.

Two groups of 6, 17-week-old (NZB×NZW)F1 female mice were injected i.p. with either saline or 1 mg/mouse of nucleoside-D-EK each day for three days. Seven days later the mice were bled. Two weeks later the treatment was repeated. Seven days later the mice were bled. Sera from the first and second bleedings were tested for anti-ssDNA antibodies using the following antigen specific ELISA protocol.

The ssDNA is immobilized in wells of polystyrene plates and is reacted with antibodies in the sera of lupus MRL (1 pr/1 pr) mice. The anti-ssDNA antibodies are visualized by addition of enzyme-linked antibodies specific for the isotypes of immunoglobulins bound to ssDNA on the plate. Subsequent addition of enzyme substrate results in a color reaction that is read in a spectrophotometer.

The ssDNA is prepared from calf thymus dsDNA. The calf thymus dsDNA obtained commercially is treated with S-1 nuclease to obtain homogenous dsDNA. The dsDNA is boiled for 5 min in a water bath and quickly cooled in an ice-water bath. Each ssDNA batch is prepared just before use in the experiment.

Ninety six-well flat bottom plates are exposed to ultraviolet (UV) light overnight in a Steril Gard Hood before use. The wells in the plates are coated overnight at 4° C. with 100 μl of ssDNA at a concentration of 1 μg/ml in saline containing 10 μg/ml methylated bovine serum albumin. The next morning, the plates are washed once in phosphate buffered saline (PBS) and are then blocked by placing 200 μl of 1% bovine serum albumin in PBS (PBSA) in each well for 45 min at 37° C. After blocking, the plates are washed twice in PBS and flicked dry. Then, 100 μl of serial dilutions of test and control sera diluted in 1% PBSA containing 0.5% Tween-20 are placed in appropriate wells. The plates are incubated for 1 hr at 37° C. Then these are washed 5 times in PBS and flicked dry followed by addition of one hundred microliters of alkaline phosphatase-conjugated goat anti mouse (IgG, A and M) antibody. The plates are incubated for another hour at 37° C. The plates are washed 7 times in PBS and flicked dry. Then, 50 μl of enzyme substrate is added and plates are incubated at room temperature for ½ hr. The reaction is stopped by addition of 50 μl of 0.2M disodium hydrogen phosphate, pH 8.6. The optical density value at 550 nm is determined for each well with a Titertek Spectrophotometer.

The data are shown in FIG. 1. As shown, the nucleoside-D-EK had no detectable effect on the anti-ssDNA titers in the mice.

EXAMPLE 2

Testing of Polynucleotides for Binding Activity with SLE Antisera

In addition to the polynucleotides used in the invention conjugates, various other DNAs were prepared and tested for their binding activity with SLE antisera. These tests, described below, show that the reactivity of the polynucleotides of the invention conjugates was unpredictable and unexpected.

Various single-stranded and double-stranded polynucleotides were prepared by chemical synthesis and, where appropriate, enzymatic extension and/or annealing. Chemical synthesis of oligonucleotides was done on a Pharmacia Gene Assembler using a Cruachem adjustable column employing phosphite triester chemistry. The solid phase was 500-angstrom controlled-pore glass beads that were derivatized with the appropriate 3'-ribo or 3'-deoxynucleotide. The oligonucleotides were purified by simple dialysis. In the case of oligonucleotides of length greater than 70 bases, individual strands were phosphorylated using ATP and rT4 polynucleotide kinase. After desalting on a Pharmacia PD10 column, the phosphorylated strands were covalently coupled using rT4 DNA ligase. All strands shared a common CATG 5' end sequence that provided a unique sticky end. Where appropriate, single strands were annealed to form dsDNA.

Two assays were employed to determine the binding of the polynucleotides with lupus antisera (1) a modified Farr assay in which radiolabeled DNA is precipitated from solution after it is bound to antibody and (2) an ELISA. In the former 25 μl of each antiserum dilution were first prepared in Tris-buffered saline (TBS, 0.15M NaCl, 0.01M Tris, pH 7.5)containing 0.1 mg/ml human gamma globulin. These were diluted with 125 μl of TBS, 50 μl of $^{125}$I-dsDNA (Diagnostics Products Los Angeles, Calif.) was added to each sample, and the samples incubated at 37° C. for ½ hr. Then 500 μl of 79% saturated $(NH_4)_2SO_4$ was added, the sample was incubated at 4° C. for 15 min and centrifuged. Radioactivity of the precipitate was measured in a gamma counter. The amount of radioactivity was a direct measure of the antibody concentration in solution. In the ELISA, plate wells were coated at 4° C. with 100 μl of dsDNA at 10 μg/ml in saline containing 10 μg/ml methylated BSA. The wells were washed with PBS and then blocked by placing 200 μl of 1% BSA in PBS (PBSA) on each well for 45 min at 37° C. The plates were again washed with PBS. Then 100 μl of test sera diluted in 1% PBSA containing 0.5% Tween 20 were added. For inhibition studies the inhibitor (e.g., polynucleotide) was also added. The plates were then incubated 1 hr at 37° C. and washed with PBS. Alkaline phosphatase-labelled goat antibody, 100 μl/well, was added and the plates incubated for another hr at 37° C. The plates were then washed, substrate was added, and the plates were incubated at room temperature for ½ hr. The reaction was stopped by adding disodium hydrogen phosphate and the plates were read with a spectrophotometer.

Tables 1 and 2 below list, respectively, various single-stranded polynucleotides and double-stranded polynucleotides that did not inhibit significantly dsDNA binding by SLE auto-antibodies in these tests.

TABLE 1

SINGLE-STRANDED NUCLEOTIDE HOMOPOLYMERS WHICH BELOW 500nM DID NOT SIGNIFICANTLY INHIBIT dsDNA BINDING TO MURINE (MRL) OR HUMAN SLE AUTO-ANTIBODIES

| composition | n-mer | composition | n-mer |
|---|---|---|---|
| A. Homopurines | | | |
| poly d(G)n | 1219* | poly d(A)n | 390* |
| | 350* | | 60 |
| | 32 | | 32 |
| | 22 | | 22 |

TABLE 1-continued

SINGLE-STRANDED NUCLEOTIDE HOMOPOLYMERS WHICH BELOW 500nM DID NOT SIGNIFICANTLY INHIBIT dsDNA BINDING TO MURINE (MRL) OR HUMAN SLE AUTO-ANTIBODIES

| composition | n-mer | composition | n-mer |
|---|---|---|---|
| | 12 | | 12 |
| | 6 | | 6 |
| | 3 | | 3 |
| B. Homopyrimidines | | | |
| poly d(C)n | 329* | poly d(T)n | 229* |
| | 60 | | 60 |
| | 30 | | 30 |
| | 24 | | 22 |
| | 22 | | 6 |
| | 12 | | 3 |
| | 6 | | |
| | 3 | | |

*Synthesized enzymatically, using rT4 DNA polymerase. Because the molecular weights are a distribution, the values of n for the enzymatically synthesized oligomers are a weight average number, estimated from the Sw,20 value of each.

TABLE 2

EXAMPLES OF OLIGONUCLEOTIDE DUPLEXES UP TO 32 BASE PAIRS LONG WHICH BELOW 500 nM DO NOT SIGNIFICANTLY INHIBIT BINDING OF dsDNA TO MURINE (MRL) OR HUMAN SLE AUTOANTISERA

A. HOMOPOLYMERS
Regular
Examples: $[A]_{30}:[T]_{30}$, $[G]_{25}:[C]_{25}$, $[I]_{20}:[C]_{20}$
B. HETEROPOLYMERS
1. Self-Aligning
Example: $[G]_2—[A]_{10}—[C]_2:[G]_2—[T]_{10}—[C]_2$
2. Repeating Dimers
Examples: $[AT]_{16}:[AT]_{16}$, $[AC]_{10}:[GT]_{10}$
3. Repeating Trimers
Examples: $[TTC]_8:[GAA]_8$, $[TTG]_8:[CAA]_8$
4. Repeating Tetramers
Example: $[ACGT]_6:[ACGT]_6$

TABLE 3

EXAMPLES OF OLIGONUCLEOTIDE DUPLEXES WHICH BELOW ABOUT 500 NM ($I_{50}$ LESS THAN 500 NM) SIGNIFICANTLY INHIBIT BINDING OF dsDNA TO HUMAN SLE SERUM AND MURINE (MRL) SERUM

| Composition | n Greater Than | Oligomer Length |
|---|---|---|
| $d(AC)_n:d(TG)_n$ | 20 | 40 or greater |
| $d(AT)_n:d(TA)_n$ | 20 | 40 or greater |
| $d(IC)_n:d(CI)_n$ | 20 | 40 or greater |
| $d(AC)_n:d(TG)_n$ | 20 | 40 or greater |
| $d(AG)_n:d(TC)_n$ | 20 | 40 or greater |
| $d(ATC)_n:d(GAT)_n$ | 15 | 45 or greater |
| $d(TAC)_n:d(GTA)_n$ | 15 | 45 or greater |

EXAMPLE 3

Correlation of Binding Activity with CD Spectrum

CD spectral measurements were carried out on poly(AT):poly(AT) of about 228 bp in length (exemplary of A-DNA), poly(GC): poly(GC) of approximately 330 bp in length (exemplary of Z-DNA) salmon sperm DNA of average length greater than 1200 bp (an example of native DNA having a B-DNA type helical configuration) and the $(AC)_{30}:(TG)_{30}$ duplex described above. SLE antisera binding assays on these oligonucleotides and DNA were carried out using the modified Farr assay as above.

All DNAs and oligonucleotides were dissolved in standard buffer (0.15M NaCl, 0.01M sodium citrate, pH 7.0) and their relative abilities to bind to H-SLE autoimmune sera were compared to their respective capacities to absorb right- and left-hand circularly polarized monochromatic light (CD spectroscopy). Serological data are expressed as ability to inhibit dsDNA binding to the sera; spectra are presented as molar ellipticity per nucleotide residue:

$$[\theta] = 100/c\cdot L$$

where $\theta$ is the observed ellipticity in degrees, L is the cell path length in cm and c is the concentration in moles of nucleotide per liter.

Figure 2:
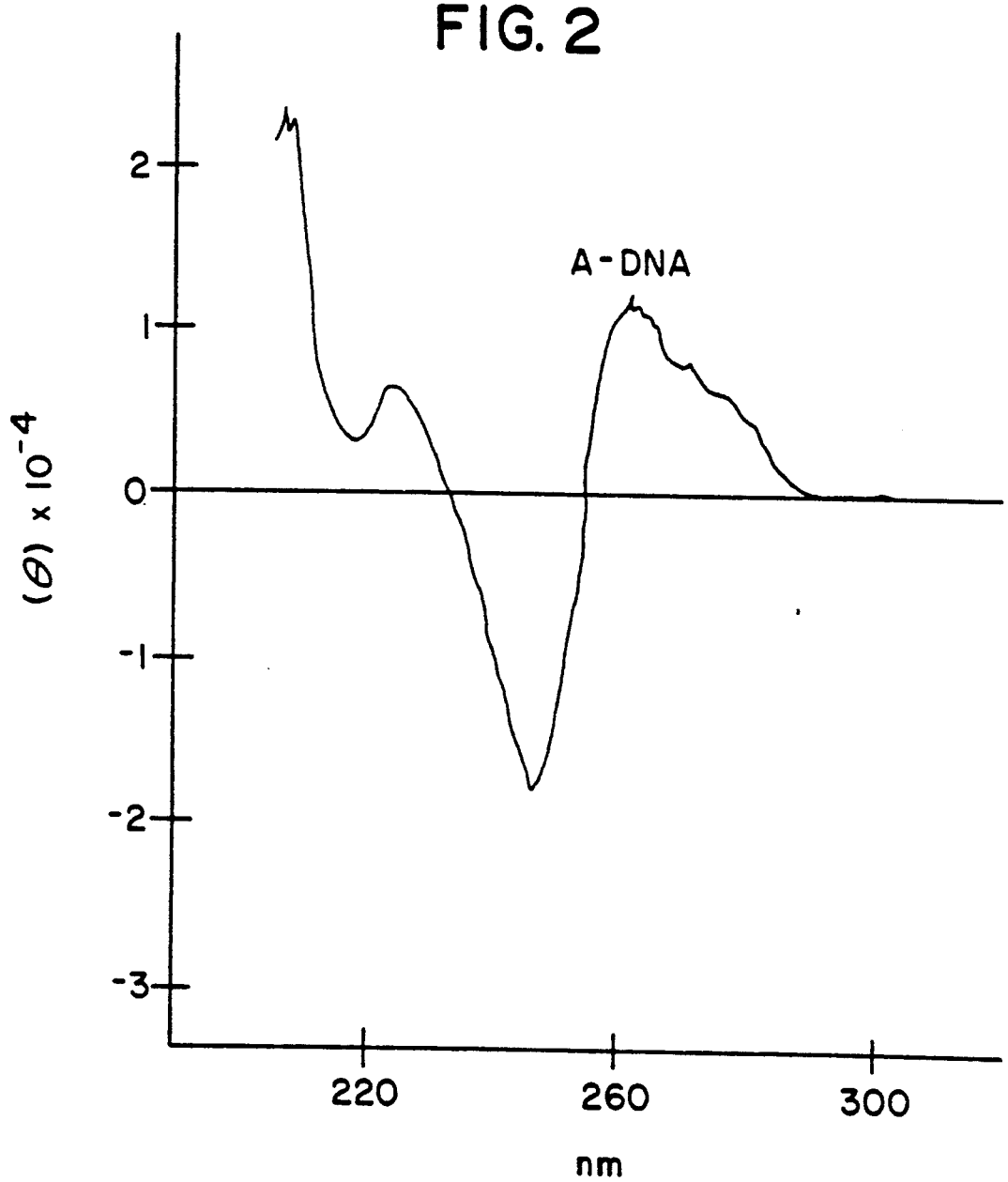
FIGS. 2 and 3 are reproductions of the CD spectra described in Example 3.

FIG. 2 shows the CD spectrum of the poly(AT):poly(AT).

Figure 3:
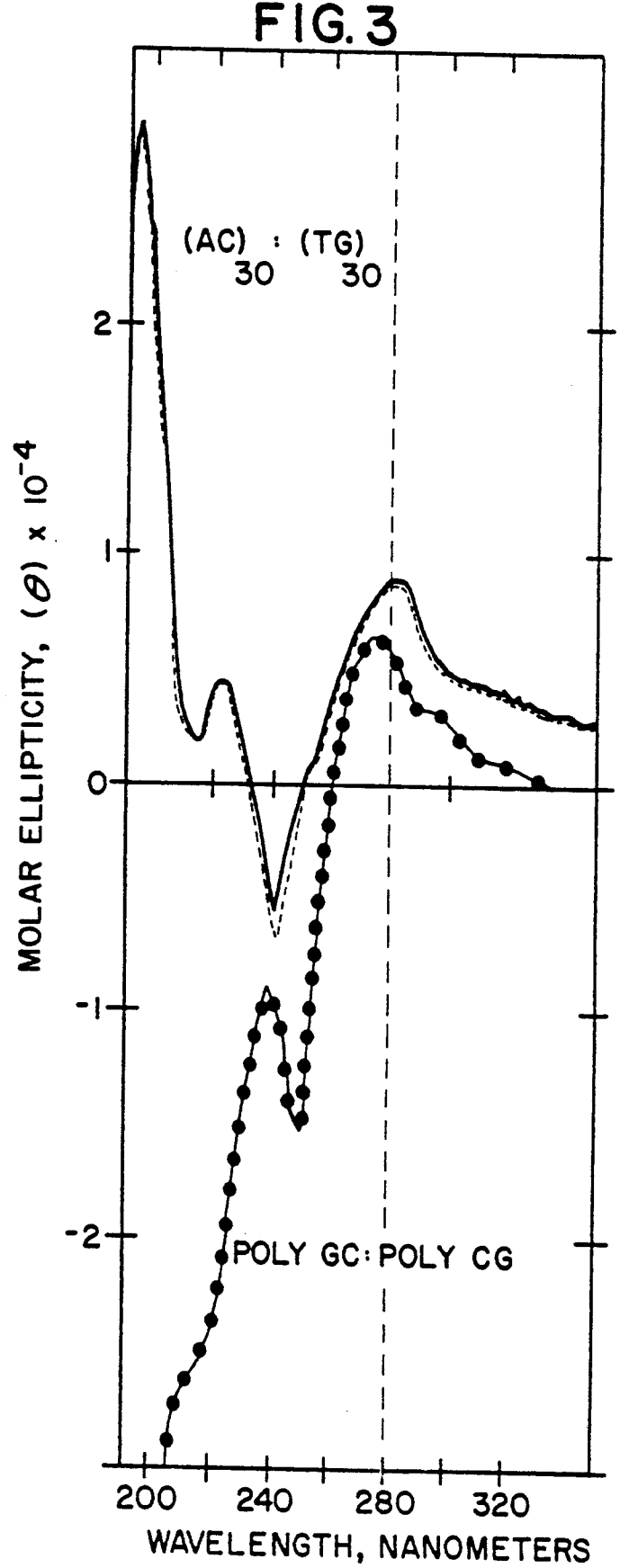

FIG. 3 shows the CD spectra of the poly(GC):poly(GC) (solid line interrupted with solid circles), the salmon sperm DNA (dashed line), and the $(AC)_{30}:(TG)_{30}$ duplex (solid continuous line).

Figure 4:
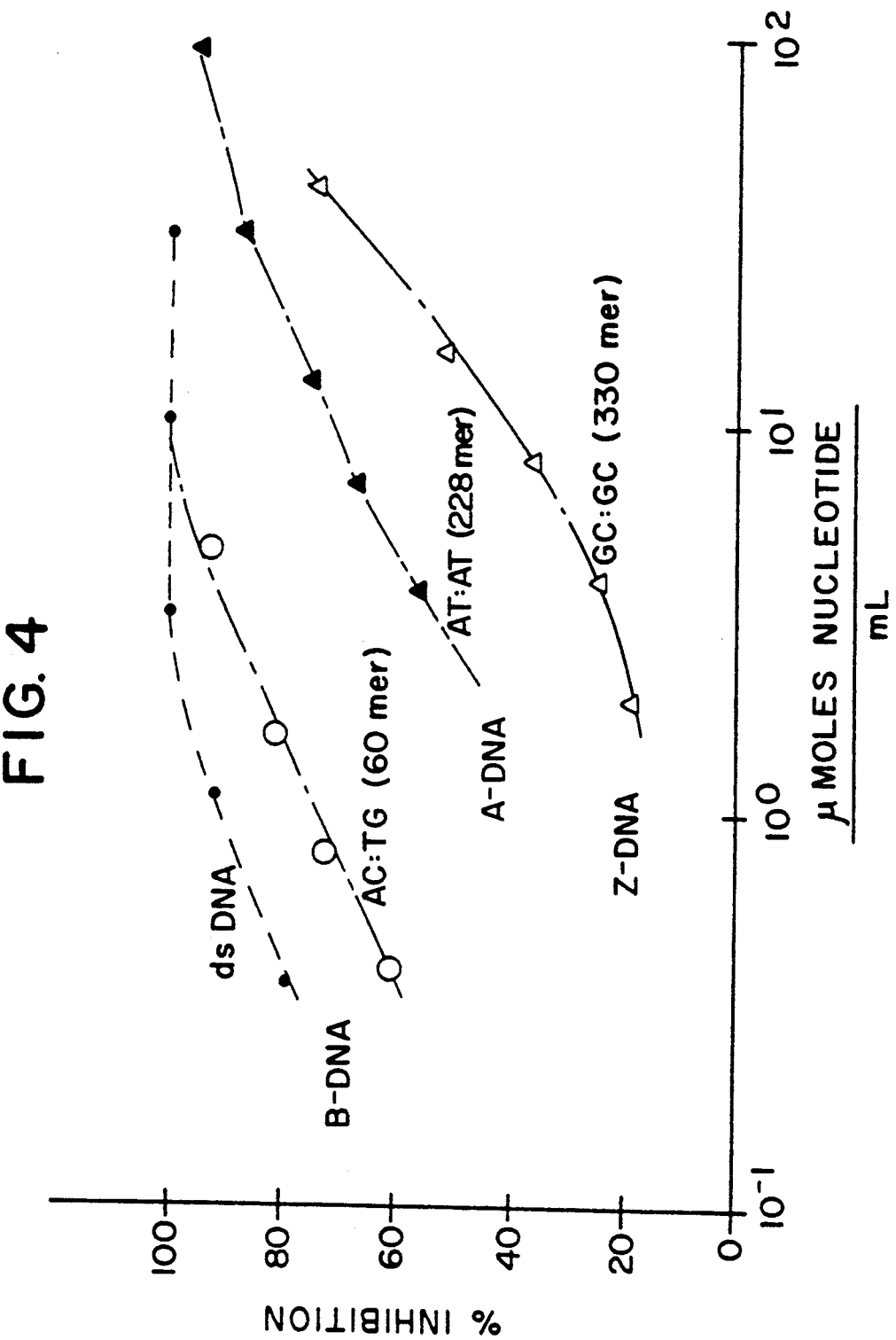
FIG. 4 is a graph comparing the SLE antisera binding capabilities of DNAs having different types of helical configuration.

FIG. 4 shows the relative capacities of the different forms of DNA to bind SLE antisera. As shown the synthetic B-type DNA had similar reactivity to native B-type DNA (calf thymus DNA was used) and substantially greater reactivity than either A-type or Z-type DNA. (Helical typing was characterized by CD spectra and, as indicated above, may not be conclusive.)

EXAMPLE 4

Synthesis of $(AC)_{30}:(TG)_{30}$-D-EK Conjugate

Based on binding activity and stability the $(AC)_{30}:(TG)_{30}$ duplex described above was selected for tolerogenic studies. A conjugate of this duplex and D-EK copolymer was prepared using the preferred synthesis procedure outlined above. The details of this synthesis follow.

D-EK copolymer, E:K mol ratio 60:40, $MW_{avg} = 30,000$ daltons was prepared from material obtained from BioMakor, Rehovet, Israel. This copolymer was dialyzed against 0.1M $KHCO_3$, pH 9.5, in dialysis tubing with a molecular weight cutoff of 25,000 daltons to a final concentration of 20 mg/ml as determined by absorbance at 220 nm in a 1 cm cuvette, where $$D\text{-}EK\ mg/ml = \frac{A_{220}\ (30{,}000\ mg/mmol)}{(168{,}000\ mL/cm\ mmol)}$$

$(AC)_{30}$ was synthesized on a DNA synthesizer and dialyzed against deionized water in dialysis tubing with a molecular weight cutoff of 12,000–14,000 daltons. The resulting solution is adjusted to a final concentration of 35 mg/ml as determined by absorbance at 260 nm in a 1 cm cuvette, where $$(AC)_{30}\ mg/ml = \frac{A_{260}\ (18{,}106\ mg/mmol)}{(458{,}160\ ml/cm\ mmol)}$$

An aqueous solution of sodium periodate, 0.1M, and water was added to the $(AC)_{30}$ to give a reaction mixture having a 5:1 molar excess of periodate to DNA. The mixture was stirred well and then placed at 4° C. for 15 min. Excess periodate was then precipitated by adding an excess of potassium chloride and the precipitate was removed by centrifugation.

A solution of D-EK and sodium cyanoborohydride was pipetted into a polypropylene reaction vessel and the pH was adjusted to between 6.0 and 8.0. The oxidized $(AC)_{30}$ was added dropwise to the D-EK in a weight ratio of 6.035:1 (10:1 molar conjugation ratio) with vigorous stirring over 24-48 hours at 4° C. After condensation, solid sodium borohydride was added to the reaction mixture, with stirring, until a final concentration of 1.0 mg/ml was reached. The reaction vessel was loosely capped and was allowed to stand, unstirred, for at least 30 min. The reaction mixture was then transferred to dialysis tubing with a 50,000 dalton cutoff and was dialyzed extensively against 0.2M sodium citrate, pH 5.0, at 4° C.

The conjugate was then purified on a Sephacryl S-200 gel permeation chromatography column in 0.2M sodium phosphate, 0.5M sodium chloride, pH 7.2. Fractions were analyzed for oligonucleotide concentration by $OD_{260}$, and for D-EK concentration by a trinitrobenzene sulfonate assay (Albers, R. W., et al., *Analyt Biochem* (1983) 137:437-443). Separation of the conjugate from free oligonucleotide was assessed by $^{32}$p-kinase labeling of the 5' hydroxyl on the oligonucleotide strand, followed by a 10% polyacrylamide, 8M urea sequencing gel and autoradiography. The gel was cut and counted on a liquid scintillation beta counter, and those fractions exhibiting ≧95% purity were pooled and dialyzed against 0.01M sodium citrate, 0.15M sodium chloride, pH 7.0 (formulation buffer) in preparation for annealing.

$(TG)_{30}$ was prepared as described above and dialyzed against formulation buffer in the same manner as $(AC)_{30}$. The molar nucleotide concentration (MNC) of $(TG)_{30}$ was determined by measuring the absorbance at 260 nm in a 1 cm cuvette:

$$MNC\ (TG)_{30} = A_{260\ nm}/(9164\ mL/cm\ mmol).$$

MNC of the $(AC)_{30}$-D-EK conjugate was determined by measuring the absorbance of the dialyzed solution at 260 nm:

$$MNC\ (AC)_{30}\text{-}D\text{-}EK = A_{260\ nm}/(7636\ mL/cm\ mmol).$$

$(TG)_{30}$ was then annealed to the $(AC)_{30}$-D-EK conjugate as follows. An equal MNC of $(TG)_{30}$ was added to the limiting reagent of $(AC)_{30}$-D-EK in a polypropylene or glass container. The mixture was heated to >95° C. in a water bath, which was maintained between 95° and 98° C. for 10 min. The solution was then cooled slowly to room temperature at the rate of ≦10°/hour.

The annealed product is dialyzed against formulation buffer in dialysis tubing with a molecular weight cutoff of 50,000 daltons. After extensive dialysis, the final conjugate is sterile-filtered through a 0.22 um membrane. It is characterized by uv spectroscopy, high performance gel permeation liquid chromatography, polyacrylamide gel electrophoresis and thermography before sterile-filling.

EXAMPLE 5

Testing of $(TG)_{30}$:$(AC)_{30}$-D-EK Conjugate as a Tolerogen

The $(TG)_{30}$:$(AC)_{30}$-D-EK conjugate described above was tested in the MRL (1 pr/1 pr) murine model for human SLE. A genetic defect in this mouse strain leads to hyperproliferation of helper T cells that, in all likelihood, participate in autoreactive B-cell differentiation. This results in secretion of autoantibodies to DNA as well as a plethora of other autoantibodies. As indicted previously, antibodies to dsDNA are a hallmark of human SLE and their presence correlates well with disease severity and renal pathology in humans.

The conjugate was diluted in saline to desired concentration for i.p. injection into mice. Four groups of five 12- to 14-week-old mice each were used. The mice were bled in the morning on day 1 and injected in the afternoon. Thereafter the mice were bled in the morning and injected in the afternoon each week for five more weeks. At weeks 6 and 7 the mice were only bled. Group 1 (control) was injected with 0.3 mg D-EK copolymer/week/mouse; Group 2, with 0.1 mg of the conjugate/week/mouse; Group 3, with 0.3 mg of the conjugate/week/mouse; and Group 4, with 1.0 mg of the conjugate/week/mouse.

Figure 5:
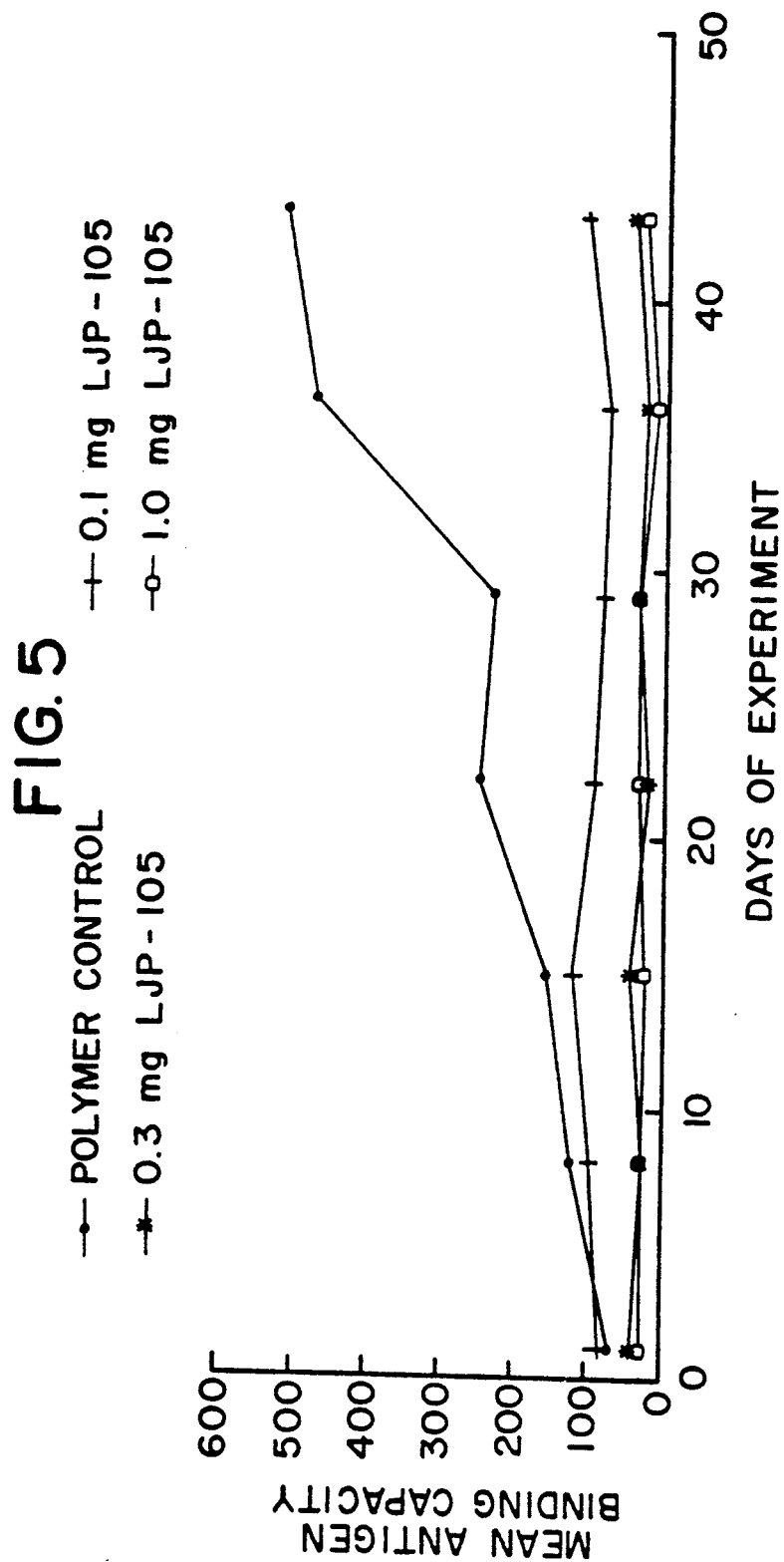

The plasma samples collected from the mice were diluted 1:10 and 1:50 in Tris buffer (0.1M, pH 7.4) and used in the modified Farr assay described above using $^3$H-dsDNA instead of $^{125}$I-dsDNA to determine the anti-dsDNA antibody titer of the samples. The data obtained in the modified Farr assay were converted into antigen binding capacity and are depicted in FIG. 5 (the conjugate is designated LJP-105).

Four weeks after termination of treatment, two mice from each group and one remaining mouse from the control group were sacrificed and levels of secretion of anti-dsDNA antibodies in each group were determined in a spleen cell ELISA where $1 \times 10^6$ to $1.5 \times 10^4$ spleen cells in doubling dilutions were placed in each well. The results of those tests are reported in FIG. 6.

A trial of the conjugate was also carried out in older MRL mice, aged 22 to 24 weeks. Again, the mice were dosed i.p. once a week, for four weeks. The serological levels of anti-dsDNA were determined after the month of treatment, and were compared to the prebleed values obtained at the start. These data, expressed as a percent change in antigen binding capacity (ABC) for individual mice, are shown in FIG. 7. FIG. 7a shows the mean data from these tests. The variability in mice per dosage group (conjugate: 0.01, 0.1, 0.3 and 1.0 mg/mouse; control mice received a mixture of polymer carrier and unconjugated nucleic acid surrogate) reflects the deaths during the experiment.

Data from the spleen cell assay from the therapeutic experiment are presented in FIG. 8, again demonstrating a significant difference between control and conjugate-treated mice, and confirming the previous serological results. As a control experiment, it was shown that soluble dsDNA inhibited the spleen cell assay. Additionally, adding spleen cells from polynucleotide-treated animals to control spleen cells did not decrease the color; rather, the effect was additive, thus ruling out that cell-bound conjugate was inhibiting the assay.

Finally, it was shown that the conjugate may be efficacious by i.p., i.m. and i.v. routes. Twenty-two-week, female MRL mice were dosed with 0.1 mg of conjugate per week for four weeks, and the percent change in antigen-binding capacity for anti-dsDNA measured. Although the control mice did not increase as much as has been seen with other experiments, there were significantly higher titers of anti-dsDNA in subcutaneously dosed mice on the one hand, and mice dosed with the conjugate by i.p., i.m. or i.v. routes on the other.

EXAMPLE 6

This example illustrates alternative procedures for making the $(AC)_{30}$:$(TG)_{30}$-D-EK conjugate.

Cloning of 60-mers

Molecular cloning is used to make 60-mers by the following protocol. A 64-mer consisting of the sequence 5'AATTC(GT)$_{29}$G3' and a second 64-mer of the sequence 5'TCGAC(AC)$_{29}$G3' are synthesized and phosphorylated by standard methods. The oligomers are mixed in equal molar ratios and slow cooled to allow duplex formation and oligomerization to occur. The overhangs of the oligomers are annealed by virtue of the 4 base overlap of the first oligomer creating an EcoRI site and the second overhang a SalI site (same as HincII site). After slow cooling, the mixture is ligated by standard methods to form an oligomer of covalently attached 60-mer units separated by either an EcoRI or SalI site. The oligomer mixture is ligated into pUC19 which had been previously digested with EcoRI and SalI. The ligation mixture is introduced into E. coli JM107 by transformation.

Ampicillin resistant colonies are picked, grown and plasmid DNA isolated. Insert size is determined by restriction digest. The desired clone has an insert which comprised at least one-half the plasmid or >50 60-mer units.

The resulting clone is grown in large scale and plasmid isolated. The plasmid is digested with EcoRI and HincII to release 60-mer with a 4 base EcoRI overhang and a blunt end at the opposite end generated by HincII. The oligomers are purified and annealed to D-EK which has the 4 base oligomer 3'TTAA-P with a 5' phosphate covalently attached to D-EK through the 3'T. The 60-mers are annealed and covalently attached to the D-EK/TTAA by ligase.

PCR Production of 60-mer

The polymerase chain reaction is used to synthesize 60-mer for coupling to D-EK by the methods described in the references cited above.

Briefly, (GT)$_{30}$ is chemically synthesized with short random sequences such as GACT and CTGA at the 5' and 3' end of (GT)$_{30}$, respectively (as illustrated below). The short random sequences are long enough to ensure proper register of the primer to the template. The primer contains the sequence of the random sequence plus several extra GT repeats as needed for stability in the annealing reaction. One of the primers also has an extra modified base at the 5' end, which allows chemical coupling to D-EK.

The PCR reaction is carried out for at least 20 cycles according to the methods cited above. The oligomers produced by PCR are purified by chromatography, such as HPLC, and then conjugated to D-EK by one of the procedures described above.

| | |
|---|---|
| PRIMER 1: | $_n$(CA)—GACT5' |
| TEMPLATE 1: | 5'*NGACT—(GT)$_{30}$—CTGA3' |
| PRIMER 2: | 5'*NGACT—(GT)$_n$ |
| TEMPLATE 2: | 3'CTGA—(CA)$_{30}$—TACG5' |

*N = modified base for D-EK coupling

EXAMPLE 7

This example illustrates the preparation of a conjugate of PEG and an oligonucleotide duplex. In this example, DMT=dimethoxytrityl; bz=benzoyl; Cp=deoxycytidine monophosphate, CE=cyanoethyl; CPG=controlled pore glass.

3,5-Bis-(iodoacetamido)benzoic acid, 1: To a stirred suspension of 572 mg (3.76 mmol) of 3,5.-diaminobenzoic acid in 19 mL of dioxane at room temperature under N$_2$ atmosphere was added 2.93 g (8.28 mmol, 2.2 eq) of iodoacetic anhydride. The mixture was stirred, covered with foil for 20 h and partitioned between 50 mL of EtOAc and 50 mL of 1N HCl solution. The EtOAc layer was washed with brine, dried over MgSO$_4$, filtered, and concentrated on a rotary evaporator to give 3.3 g of tan solid. The material was purified by silica gel chromatography (94/5/1 CH$_2$Cl$_2$/MeOH/HOAc) to yield 992 mg (54%) of 1 as a white solid: NMR (DMSO) 3.84 (s, 4 H), 7.91 (s, 2 H), 8.14 (s, 1 H), 10.56 (s, 2 H).

3.5-Bis-(iodoacetamido)benzoyl chloride. 2: To a solution of 390 mg (0.8 mmol) of 1 in 34 ml of THF was added 117 µl (1.6 mmol, 190 mg) of SOCl$_2$. The mixture was refluxed under N$_2$ atmosphere until all solids had dissolved (approx. 30 min) to give a clear red-brown solution. The mixture was concentrated on the rotary evaporator and placed under vacuum to provide crude 2 as a foamy solid which was used directly in the next step. N,N'-Bis-(3,5-bis-(iodoacetamido)benzoyl) derivative of α,ω-bis-(N-2-aminoethylcarbamoyl)polyethyleneglycol, 3 (DABA-PEG): Into a tared flask was placed 570 mg of α,ω-bis-(N-2-aminoethylcarbamoyl)-polyethyleneglycol (0.16 mmol, 3350 g/mol, Sigma). Toluene (20 mL) was added and water was removed by azeotropic distillation. The residue was dried under vacuum to give 549 mg solid and dissolved in 4 ml THF with 89 µl (0.64 mmol) of diisopropylethylamine. The crude acid chloride was dissolved in 4 ml anhydrous THF and added to the mixture over 30 sec at under N$_2$. The mixture was stirred for 16 hr at room temperature and partitioned between 25 ml of 0.1N HCl and 25 ml of CH$_2$Cl$_2$. The aqueous layer was again extracted with CH$_2$Cl$_2$ and the organic layers were combined, washed with 25 mL of H$_2$O, followed by 50 ml of at NaHCO$_3$ solution. The organic layers were dried with Na$_2$SO$_4$, filtered, and concentrated to give 784 mg of orange oil. Silica gel chromatography (9/1 CH$_2$Cl$_2$/MeOH) yielded 190 mg of colorless oil which was crystallized from hot EtOH/Et$_2$O, collected on sintered glass filter under N$_2$ pressure, and dried under vacuum to provide 177 mg of 3 as a white solid: NMR (CDCL$_3$ 3.40 (brd m, 8 H), 3.59 (brd s, (CH$_2$CH$_2$O)$_n$, integral too large to integrate in relation to other integrals), 3.80 (brd m, 4 H), 3.91 (s, 8 H), 7.49 (brd m, 2 H), 7.77 (brd m, 2 H), 7.82 (brd s, 4 H), 8.27 (brd s, 2 H), 8.90, (brd m, 4 H): iodoacetyl determination (*European Journal of Biochemistry* (1984) 140:63–71): Calculated, 0.92 mmol/g; Found, 0.96 mmol/g. This compound may be represented by the following chemical formula.

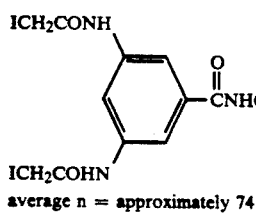
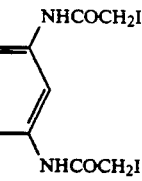

average n = approximately 74

Preparation of 5'-Modified (CA)₁₀

A synthesis of the oligonucleotide d-[DMT-(bzCp(CE)bzA)₁₀] was prepared on a Milligen 880 Prep Scale DNA synthesizer. The manufacturer's protocols for DNA phosphoramidite synthesis were followed. The synthesis was carried out on 10 gm DMT-d-bzA-CPG support. The nucleoside loading on the support was 30.0 μMoles/gm. For this type of synthesis we assume a stepwise coupling efficiency of 98% and approximately 40% overall yield of full length oligonucleotide.

After the synthesis of the twentymer was complete, the final DMT blocking group was removed using the machine protocol. Milligen activator solution, Cat. No MBS 5040 (45 ml) and 0.385 g of O-(14-(4',4''-dimethoxytriphenylmethoxy)-7,8-dithiotetradecyl) -O-(2-cyanoethyl)-N-N-diisopropylphosphoramidite (prepared as described in U.S. Ser. No. 731,055, filed 15 Jul. 1991, the disclosure of which is incorporated herein by reference) were added to the reaction and the suspension was mixed for 8 min. by Argon ebullition. Following this the oligomer was oxidized by the usual machine protocol.

The support-bound oligonucleotide was removed from the reaction vessel, air dried and treated with 100 ml concentrated ammonia for 16 h at 55° C. This step cleaves the oligomer from the CPG support, removes the cyanoethyl groups from the phosphates, and hydrolyzes the benzoyl protecting groups on the bases. This step does not remove the DMT group.

The reaction was allowed to cool and then filtered through a Gelman 10 μ polypropylene filter and washed with 200 ml 2 mm NaCl adjusted to pH 12 with NaOH. The filtrate was then applied to a Amicon chromatography column (0.45×9.4 cm, 150 ml) which had been packed with Q-Sepharose (Pharmacia). The column had been previously equilibrated with 3M NaCl and 2 mm NaCl, pH 12.

The column was eluted with a linear gradient formed from 250 ml 2 mm NaCl, pH 12 and 250 ml 1.3M NaCl, pH 12. The flow rate was then washed with 1.3M NaCl, pH 12 until all U.V. absorbing material came off.

The absorbance at 260 nm ($A_{260}$) for each tube was determined in a Perkin-Elmer Lambda 4 spectrophotometer. The U.V. absorbing fractions were further analyzed by polyacrylamide electrophoresis and those containing pure product were pooled. The pool (120 ml) was treated with 240 ml cold isopropanol and stored for 30 min at −20° C. The precipitate was collected by centrifugation in a Sorvall RC 3B centrifuge using a model H-6000A rotor for 15 min. at 3000 rpm and 4° C.

The yield of 5'-modified (CA)₁₀ was 14946 $A_{260}$ units (498 mg, 62.2 μMoles, 20% based on 300 μMoles CPG Nucleoside.)

Conjugation of 5'Modified Oligonucleotides to DABA-PEG

A solution of 11,568 $A_{260}$ units (48.2 μMoles, assume molar extinction at 260 nm=240,000) of the 5'-modified (CA)₁₀ in 7.7 ml water was treated with 1 ml 0.1M NaHCO₃ and 210 μL (876 μMoles, 18 times molar excess) tributylphosphine for 0.5 hr at room temperature. The suspension was shaken from time to time.

To remove the 6-dimethoxytrityl-1,6-1-thiohexanediol, the suspension was treated with 0.8 ml 3M NaCl and 16 ml cold isopropanol. After 30 min. at −20° C. the material was centrifuged as described previously.

The pellet was redissolved in 2 ml water, 0.2 ml 3M NaCl, treated with 4 ml isopropanol and recentrifuged. The pellet was briefly dried under vacuum.

The pellet was dissolved in 2.8 ml water and 1 ml 0.1N NaHCO₃ which had been sparged with helium. 6.7 mg DABA-PEG was added and dissolved. The reaction was kept for 16 h at room temperature in the dark.

The reaction mixture in 6 ml was applied to a 5×91 (1800 ml) Pharmacia column which was packed with Sephacryl 200 (Pharmacia). The column was eluted with 0.5M NaCl, 0.1M sodium borate, pH 8.3. A peristaltic pump was used and set to give a flow rate of approx. 2 ml per min., and fractions of 15 ml were collected. The absorbance of the fractions at 260 nm was measured. The fractions were also analyzed by polyacrylamide gel electrophoresis and those containing pure conjugate were pooled.

Hybridization of Conjugate

The pooled fractions from above contained 726 $A_{260}$ units. The equivalent amount of d-(TG)₂₀ was added and the tube was heated at 90° C. for ten minutes and then allowed to cool to room temperature over an hour and a half.

An equal amount of isopropanol was added and the mixture kept for 3 h at −20° C. After centrifugation as above, the pellet was dissolved in 0.15M NaCl, 0.01M sodium citrate, pH 6.8. 53 mg of the hybrid was obtained.

An aliquot of the material was diluted in the above buffer and the melting temperature of the duplex was determined in a Carey 3E spectrophotometer. The material had a Tm of 73.4° C. and 31.1% hyperchromicity. A 10 $A_{260}$ unit aliquot of the product was annealed with excess TG as described above. This as well as unannealed conjugate and a TG standard were analyzed by gel permeation HPLC on a Shodex Protein KW 8025 column on a Rainin HPLC instrument. The column was eluted isocratically with 0.05M NaH₂PO₄, pH 6.5, 0.5M NaCl. The run time was 12 min. The product had a retention time of 6.9 min. and TG twentymer 9.2 min. Comparison of the area under the peaks showed that 98.09% of the product was double stranded DNA.

The conjugate is represented by the formula $PEG_{3000} [DABA]_2-[S-(CH_2)_6$
$OPO_2-O-(CA)_{10}:(GT)_{10}]_4$ This conjugate is designated "ON-DABA-PEG."

Testing of ON-DABA-PEG as a Tolerogen

ON-DABA-PEG was tested for its ability to tolerize mice to the oligonucleotide $(CA)_{25}:(GT)_{25}$ in mice that had been immunized with an immunogenic form of the oligonucleotide. The immunogen is a conjugate of the oligonucleotide and KLH and may be represented by the formula $KLH-[NH(CH_2)_5OPO_2-O-(CA)_{25}:(GT)_{25}]\sim 5$ (assuming a molecular weight of $10^5$ for KLH). This immunogen is designated "ON-KLH."

Material and Methods

Mice: C57BL/6 female mice 6 weeks of age were purchased from Jackson Laboratories, Bar Harbor, Me. The mice were housed and cared for by standard methods.

Immunization: The mice were primed, according to the method of Iverson (Assay for in vivo Adoptive Immune Response in Handbook of Experimental Immunology, Vol 2 *Cellular Immunology*. Eds. D. M. Weir, L. A. Herzenberg, C. Blackwell and A. Herzenberg, 4th Edition, Blackwell Scientific Publications, Oxford) by injecting the mice, IP, with 100 μg of ON-KLH precipitated on alum and with $2 \times 10^9$ formalin fixed pertussis organisms as an adjuvant. The mice were boosted with 50 μg of ON-KLH, in saline, IP.

Coupling of ON to SRBC: Sheep Red Blood Cells (SRBC) in Alsevers were purchased from Colorado Serum Co. Denver, Colo., and used within two weeks. The SRBC were coated with $(CA)_{25}:(GT)_{25}$ (a 50 mer of CA:GT) by the method of Kipp and Miller ("Preparation of Protein-Conjugated Red Blood Cells with ECDI (Modification)" in *Selected Methods in Cellular Immunology*, (1980), Eds. B. B. Mishell and S. M. Shiigi, W. H. Freemen and Co., San Francisco, p. 103). Briefly, the SRBC were washed 4 times in cold saline, mixed with 2 mg of $(CA)_{25} (GT)_{25}$ coupled to D-EK in 0.35M mannitol, 0.01M NaCl containing 10 mg of carbodiimide and incubated for 30 minutes at 4° C. The coated SRBC were washed twice with cold Balanced Salt Solution and resuspended to 10% (v/v).

Plaque assay: The number of anti-ON plaque forming cells (pfc) was determined using the Cunningham technique (Marbrook, J., "Liquid Matrix (Slide Method)", in *Selected Methods in Cellular Immunology*, (1980), Eds. B. B. Mishell and S. M. Shiigi, W. H. Freemen and Co., San Francisco, p. 86.) The number of IgG pfc were determined by elimination of IgM plaques using rabbit and anti-mouse IgG as described by Henry ("Estimation of IgG responses by Elimination of IgM Plaques" in *Selected Methods in Cellular Immunology*, (1980), Eds. B. B. Mishell and S. M. Shiigi, W. H. Freemen and Co., San Francisco, p. 91). Briefly, spleens were harvested and single cell suspensions made in BSS. Guinea pig serum was added to oligonucleotide coated SRBC to give a final dilution of 1:9 guinea pig serum, and enough rabbit anti-mouse IgG was added to give a final dilution of 1:100 rabbit anti-mouse IgG. Equal volumes of the SRBC mixture and diluted spleen cells were mixed in microtitre wells and transferred to Cunningham chambers. Each spleen was tested individually and in triplicate. The edges of the chambers were sealed with paraffin and the chambers were incubated at 37° C. for 1 hour. The number of plaques were enumerated by viewing the chambers under an inverted microscope.

Results

Mice were primed with ON-KLH on alum with pertussis as an adjuvant and seven weeks later divided into groups of 3 mice each. The mice were treated, IP, with doubling dilution of ON-DABA-PEG, all of the mice, including the control, were boosted with 50 μg of ON-KLH, in saline, IP. Four days later, the spleens were harvested and the number of IgG pfc determined. As shown in Table 4, all doses of ON-DABA-PEG tested showed a significant reduction in the number of pfc as compared to the control group.

TABLE 4

| Tolerogenic Activity of ON-DABA-PEG | | |
|---|---|---|
| Dose (μg/mouse) | $pfc/10^6$ spleen cells Mean (S.D.) | % Reduction Mean |
| None | 12865 (2846) | |
| 62.5 | 2868 (6809) | 77.7 |
| 125 | 3331 (939) | 74.1 |
| 250 | 3044 (1929) | 76.3 |
| 500 | 1809 (759) | 85.9 |
| 1000 | 2814 (554) | 78.1 |

Modifications of the above-described modes for carrying out the invention that are obvious to those of skill in the fields of oligonucleotide chemistry, conjugation chemistry, immunology and related fields are intended to be within the scope of the following claims.

We claim:

1. A conjugate of (a) a biologically stable valency platform molecule and (b) a multiplicity of polynucleotide duplexes of at least about 20 base pairs each bound to the valency platform molecule, said duplexes each having a significant binding activity for human systemic lupus erythematosus anti-dsDNA autoantibodies.

2. The conjugate of claim 1 wherein the valency platform molecule is a polymer.

3. The conjugate of claim 2 wherein the polymer is a copolymer of D-glutamic acid (E) and D-lysine (K) or a polyethylene glycol having a molecular weight of about 1,000 to 20,000.

4. The conjugate of claim 2 wherein the duplexes are substantially homogeneous in length.

5. The conjugate of claim 4 wherein the duplexes are substantially homogeneous in nucleotide composition.

6. The conjugate of claim 2 wherein the duplexes are 20 to 50 bp in length.

7. The conjugate of claim 2 wherein the duplexes are bound to the polymer at or proximate one of their ends.

8. The conjugate of claim 7 wherein the duplexes are bound to the polymer via reaction between a functional group at or proximate a terminus of one strand of the duplex and a functional group on the polymer.

9. The conjugate of claim 2 wherein the polynucleotide duplexes are composed of complementary repeating mer units of 2 to 4 different bases.

10. The conjugate of claim 9 wherein the polynucleotide duplexes are:
   poly d(GC):poly d(CG); poly d(AT):poly d(TA);
   poly d(IC):poly d(CP); poly d(AC):poly d(TG); or
   poly d(AG):poly d(TC).

11. The conjugate of claim 2 wherein the polynucleotide duplex is $(AC)_{30}:(TG)_{30}$, and the polymer is a copolymer of D-glutamic acid and D-lysine.

12. The conjugate of claim 11 wherein the molar ratio of duplex to polymer is in the range of 2:1 to 30:1.

13. The conjugate of claim 2 wherein the polynucleotide duplex is $(CA)_{10}:(TG)_{10}$ and the polymer is polyethylene glycol.

14. The conjugate of claim 13 wherein the molar ratio of duplex to polyethylene glycol is 4:1 to 6:1.

15. A conjugate of (a) a biologically stable valency platform molecule and (b) a multiplicity of polynucleotide duplexes of at least 20 base pairs each bound to the valency platform molecule, said duplexes being substantially homogeneous in length and said conjugate being a tolerogen for human systemic lupus erythematosus.

16. The conjugate of claim 15 wherein the valency platform molecule is a polymer.

17. A conjugate of (a) a biologically stable valency platform molecule and (b) a multiplicity of polynucleotide duplexes of at least about 20 base pairs each, said duplexes each being bound to the valency platform molecule at or proximate one of their ends, said conjugate being a tolerogen for human systemic lupus erythematosus.

18. The conjugate of claim 17 wherein the valency platform molecule is a polymer.

19. A conjugate of (a) a biologically stable valency platform molecule and (b) a multiplicity of polynucleotide duplexes of at least about 20 bases pairs each bound to the valency platform molecule, said duplexes having a B-DNA type helical structure and said conjugate being a tolerogen for human systemic lupus erythematosus.

20. The conjugate of claim 19 wherein the valency platform molecule is a polymer.

21. A pharmaceutical composition for treating lupus comprising the conjugate of claim 1 formulated with a pharmaceutically acceptable injectable vehicle.

22. A pharmaceutical composition for treating lupus comprising the conjugate of claim 2 formulated with a pharmaceutically acceptable injectable vehicle.

23. A pharmaceutical composition for treating lupus comprising the conjugate of claim 11 formulated with a pharmaceutically acceptable injectable vehicle.

24. A pharmaceutical composition for treating lupus comprising the conjugate of claim 12 formulated with a pharmaceutically acceptable injectable vehicle.

25. A pharmaceutical composition for treating lupus comprising the conjugate of claim 13 formulated with a pharmaceutically acceptable injectable vehicle.

26. A pharmaceutical composition for treating lupus comprising the conjugate of claim 14 formulated with a pharmaceutically acceptable injectable vehicle.

27. A method for treating an individual for lupus comprising administering a therapeutically effective amount of the conjugate of claim 1 to the individual in need of such treatment.

28. A method for treating an individual for lupus comprising administering a therapeutically effective amount of the conjugate of claim 2 to the individual in need of such treatment.

29. A method for treating an individual for lupus comprising administering a therapeutically effective amount of the conjugate of claim 11 to the individual in need of such treatment.

30. A method for treating an individual for lupus comprising administering a therapeutically effective amount of the conjugate of claim 12 to the individual in need of such treatment.

31. A method for treating an individual for lupus comprising administering a therapeutically effective amount of the conjugate of claim 13 to the individual in need of such treatment.

32. A method for treating an individual for lupus comprising administering a therapeutically effective amount of the conjugate of claim 14 to the individual in need of such treatment.

33. A method for making the conjugate of claim 2 comprising:
  (a) bonding a multiplicity of single-stranded polynucleotides of at least about 20 base pairs each, each of which has a reactive functional group at or proximate one of its termini with functional groups on the polymer to form a conjugate; and
  (b) annealing complementary single-stranded polynucleotides to the single-stranded polynucleotides conjugated to the polymer to form said duplexes.

* * * * *